United States Patent [19]

Ekechukwu

[11] Patent Number: 5,489,536
[45] Date of Patent: Feb. 6, 1996

[54] DETECTION OF CHLORINATED AROMATIC COMPOUNDS

[75] Inventor: Amy A. Ekechukwu, Augusta, Ga.

[73] Assignee: The United States of America as represented by the Department of Energy, Washington, D.C.

[21] Appl. No.: 304,975

[22] Filed: Sep. 13, 1994

Related U.S. Application Data

[63] Continuation-in-part of Ser. No. 22,579, Feb. 23, 1993, abandoned.

[51] Int. Cl.$^6$ ............................. G01N 21/64; G01N 21/76
[52] U.S. Cl. ............................. 436/169; 436/172; 422/52; 422/57; 422/82.08
[58] Field of Search ..................... 422/52, 57, 82.07, 422/82.08; 252/301.6; 436/169, 172; 250/461.1

[56] References Cited

U.S. PATENT DOCUMENTS

| | | | |
|---|---|---|---|
| 4,548,907 | 10/1985 | Seitz et al. | 436/163 |
| 4,577,109 | 3/1986 | Hirschfeld | 250/461.1 |
| 4,666,672 | 5/1987 | Miller et al. | 422/68 |
| 4,929,562 | 5/1990 | Anderson et al. | 436/126 |
| 4,934,811 | 6/1989 | Watts et al. | 356/73 |
| 5,019,350 | 5/1991 | Rhum et al. | 422/82.07 |
| 5,034,189 | 7/1981 | Cox et al. | 422/52 |
| 5,037,615 | 8/1991 | Kane | 422/82.08 |
| 5,045,282 | 9/1991 | Kritzman et al. | 422/56 |
| 5,047,627 | 9/1991 | Yim et al. | 250/227.3 |
| 5,081,041 | 1/1992 | Yafuso et al. | 436/68 |
| 5,093,266 | 3/1992 | Leader et al. | 436/68 |
| 5,119,463 | 6/1992 | Vurek et al. | 385/129 |
| 5,143,066 | 9/1992 | Komires et al. | 128/634 |
| 5,219,527 | 6/1993 | Hui et al. | 422/82.06 |
| 5,220,172 | 6/1993 | Berthold et al. | 250/461.1 |

Primary Examiner—Robert J. Warden
Assistant Examiner—N. Bhat
Attorney, Agent, or Firm—Brian R. Tumm; Harold M. Nixon; William R. Moser

[57] ABSTRACT

A method for making a composition for measuring the concentration of chlorinated aromatic compounds in aqueous fluids, and an optical probe for use with the method. The composition comprises a hydrophobic polymer matrix, preferably polyamide, with a fluorescent indicator uniformly dispersed therein. The indicator fluoresces in the presence of the chlorinated aromatic compounds with an intensity dependent on the concentration of these compounds in the fluid of interest, such as 8-amino-2-naphthalene sulfonate. The probe includes a hollow cylindrical housing that contains the composition in its distal end. The probe admits an aqueous fluid to the probe interior for exposure to the composition. An optical fiber transmits excitation light from a remote source to the composition while the indicator reacts with chlorinated aromatic compounds present in the fluid. The resulting fluorescence light signal is reflected to a second optical fiber that transmits the light to a spectrophotometer for analysis.

10 Claims, 1 Drawing Sheet

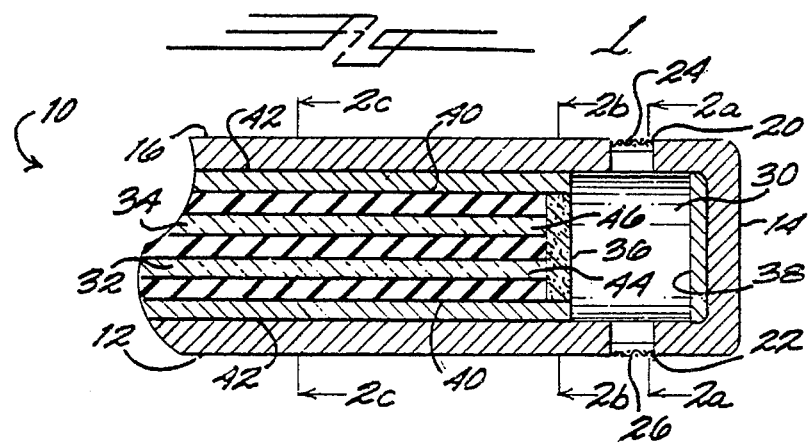
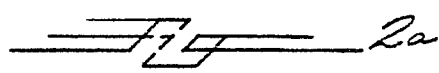
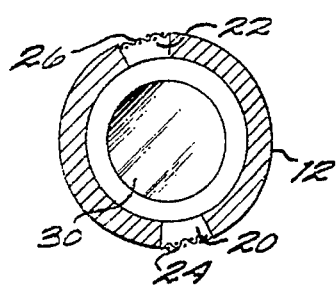
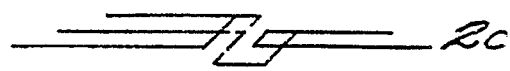
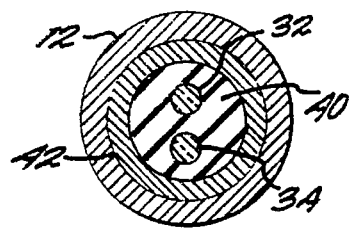
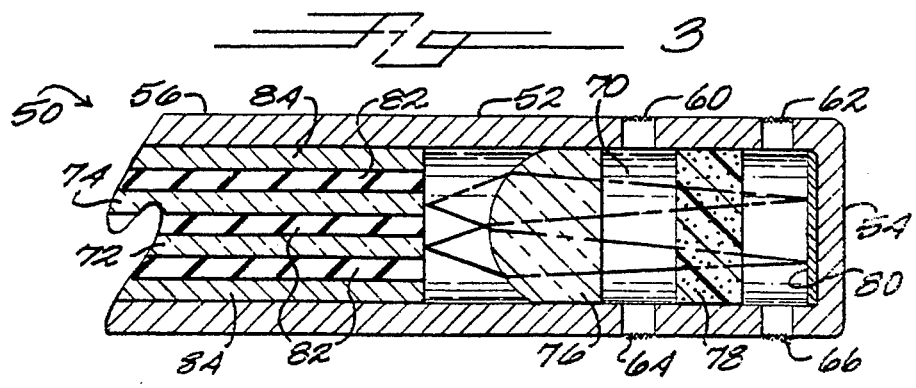

DETECTION OF CHLORINATED AROMATIC COMPOUNDS

The United States Government has rights in this invention pursuant to Contract No. DE-AC09-89SR18035 between the U.S. Department of Energy and Westinghouse Savannah River Company. This is a Continuation-In-Part of application Ser. No. 08/022,579 filed Feb. 23, 1993 now abandoned.

BACKGROUND OF THE INVENTION

1. Field of the Invention

The present invention relates to the detection of chlorinated aromatic compounds in aqueous fluids. More particularly, the present invention relates to a method for measuring the concentration of chlorinated aromatic compounds in an aqueous fluid, and a composition and fiber optic probe for measuring that concentration.

2. Discussion of Background

Fiber optic probes for detecting various substances are well known. Such devices, whether intended for continuous remote operation or occasional laboratory analyses, are typically a solution containing an indicator responsive to the presence of the substance of interest (analyte). The presence of the analyte results in a change in the optical properties of the indicator, such as its color, the intensity of light it transmits, and its fluorescence emission spectrum. There is a wide selection of indicators for detection and analysis of corresponding analytes. For example, indicators are available for the qualitative and quantitative detection of oxygen, carbon dioxide, hydrogen ions (pH), glucose, ammonia, and certain metal ions.

Fiber optic-based detecting systems using spectrometric analysis techniques generally include a light source, a sample cell formed to admit a fluid containing the analyte of interest, an indicator, optic fibers for transmitting light to and from the sample cell and a light analyzer such as a spectrophotometer. Light is transmitted through the sample cell and received by the spectrophotometer, which reveals the spectrum of the received light. Fiber optic light transmitting fibers are favored in devices for remote operation. Further, a plurality of optical probes may be connected to a single light source and detector, as in the remote multi-position information gathering system described by Hirschfeld (U.S. Pat. No. 4,577,109).

Numerous methods exist for securing the indicator within such a probe. The indicator is usually immobilized in a polymer matrix by absorption or adsorption to form a composition. Preferably, the indicator is bound to the matrix so that the composition may be in contact with the fluid without loss of the indicating substance. The polymer matrix is preferably permeable to the fluid so that the analytes can reach the active sites bearing the indicator molecules. In general, the faster the fluid permeates the matrix, the shorter the response time of the probe.

The sensitivity and specificity of the probe are determined in part by the type and amount of the indicator present in the matrix. Preferably, the indicator is sensitive to the analyte but not to other chemical species the fluid might contain. The matrix is substantially optically transparent in the wavelength range for fluorescent excitation and emission of the indicator.

Specific examples of fluorescence indicators include U.S. Pat. No. 5,037,615, issued to Kane for a sensor unit with a fluorescence energy transfer indicator for measuring pH, oxygen and carbon dioxide concentrations, and metal ions. The indicator is contained in a porous glass plug at the distal (working) end of an optical fiber. Kritzman, et al. (U.S. Pat. No. 5,045,282) show a sensor having a substantially non-porous glass tip fused to or integral with an open end of glass optical fiber. A fluorescent substance is adsorbed on the internal surfaces of the pores; the tip is coated with a porous polymeric film prior to use. Suitable fluorescent materials include coumarin derivatives (pH and $CO_2$ determination), and pyrene and other polycyclic aromatic compounds ($O_2$ determination). Yafuso, et al. (U.S. Pat. No. 5,081,041) disclose a two-layer sensor for detecting hydrogen or hydroxyl ions (pH) in fluids. The sensor includes a fluorescence and pH indicator such as hydroxypyrene trisulfonic acid or derivatives thereof. Cox, et al. (U.S. Pat. No. 5,034,189) immobilize a fluorophor in a permeable, transparent polymeric matrix. When the matrix is exposed to the fluid being analyzed, the intensity of the fluorescent radiation is proportional to the concentration of the analytes in the fluid. For analyzing oxygen, 9,10 diphenyl anthracene is incorporated into a poly (dimethyl siloxane) or silicone matrix. For analyzing glucose concentration, 9,10-diphenyl anthracene in a poly (hydroxyethyl methacrylate) is used. Rhum, et al. (U.S. Pat. No. 5,019,350) disclose fluorescent polymers for the determination of blood gas or pH. Fluorescent organic substituents are covalently bonded to an organic, water-insoluble polymer through ester or amide linkages. Suitable polymers include hydroxyethyl methacrylate homopolymer, polyvinyl alcohol, and so forth. Suitable fluorescent indicators for blood oxygen include the pyrene butyric acids; indicators for pH include 4-(carboxymethyl) umbelliferone (CMU).

Despite the existence of fiber optic probes using well known indicators, it is believed that no detector exists for effectively detecting small concentrations of chlorinated aromatics, including polychlorinated biphenyls (PCBs). The detection of low levels of PCBs, particularly in groundwater, is a growing concern in environmental monitoring, thus, there is an immediate need for detectors of this kind. A satisfactory detector for the detection and measurement of chlorinated aromatics, including PCBs, should be sensitive to trace amounts (1 ppb or less), have a short response time, long-term stability and reproducibility, and be chemically inert to the operating environment.

SUMMARY OF THE INVENTION

According to its major aspects and broadly stated, the present invention is a composition and method for detecting the presence and concentrations of chlorinated aromatic compounds in aqueous fluids. The composition comprises a fluorescent indicator dispersed throughout a polymer matrix. When the indicator comes into contact with chlorinated aromatic compounds, it fluoresces with an intensity proportional to the concentration of the compounds. The composition is positioned in an optical probe. The probe admits a sample of a fluid through openings in the probe housing, allowing the fluid to contact the composition. A first optical fiber transmits light of a suitable wavelength to the probe so that it can pass through the fluid that has interacted with the composition and cause any chlorinated aromatic compounds present to fluoresce. Fluorescence emitted by the composition is reflected by a mirror to a second optical fiber that transmits the emitted light to a detector such as a spectrophotometer. The spectrum produced by the spectrometer is analyzed to determine the concentration of chlorinated aromatics in the fluid.

An important feature of the present invention is the indicator. A suitable indicator for use with the composition is 8-amino-2-naphthalene sulfonate, which fluoresces in the presence of chlorinated aromatic compounds including polychlorinated biphenyls (PCBs). The indicator is supplied in an amount sufficient to provide a concentration-dependent signal of sufficient intensity to be analyzed in determining the concentration of chlorinated aromatic compounds in the fluid.

Another feature of the present invention is the combination of the indicator and a hydrophobic polymer matrix. The matrix is at least partly permeable to the fluid in order to facilitate contact of the indicator with chlorinated aromatics in the fluid so that fluorescence can occur. The polymer is substantially optically transparent at the fluorescence excitation and emission wavelengths of the indicator. Preferably, the matrix is a polyamide or other polymer that is permeable, optically transparent, and is easy to use in manufacturing the probe.

Still another feature of the present invention is the optical probe with which the composition is used. The probe preferably has the two optical fibers entering from the same end of the housing, adjacent and parallel to each other, a first fiber for transmitting excitation light to the composition and a second fiber for transmitting the resulting fluorescence signal to a detector for analysis. A mirror is positioned in the probe to reflect light from the first fiber to the second fiber once it has crossed the composition. A lens may be added to focus the light if desired.

Other features and advantages of the present invention will be apparent to those skilled in the art from a careful reading of the Detailed Description of a Preferred Embodiment presented below and accompanied by the drawings.

BRIEF DESCRIPTION OF THE DRAWINGS

In the drawings,

FIG. 1 is a side cross-sectional view of an optical probe according to a preferred embodiment of the present invention;

FIG. 2a is a partial cross-sectional view of the probe taken along lines 2a—2a of FIG. 1;

FIG. 2b is a partial cross-sectional view of the probe taken along lines 2b—2b of FIG. 1;

FIG. 2c is a partial cross-sectional view of the probe taken along lines 2c—2c of FIG. 1; and FIG. 3 is a side cross-sectional view of an optical probe according to an alternative preferred embodiment of the present invention.

DETAILED DESCRIPTION OF A PREFERRED EMBODIMENT

A composition for detecting chlorinated aromatic compounds comprises generally a polymer matrix material having a fluorescent indicator dispersed therein. When contacted by an aqueous fluid containing chlorinated aromatic compounds, the indicator fluoresces with an intensity proportional to the concentration of chlorinated aromatics in the fluid.

When cured, the matrix material is at least partly permeable to the fluid of interest in order to facilitate contact of the indicator with chlorinated aromatics in the fluid. It is substantially optically transparent at the fluorescence excitation and emission wavelengths of the indicator, so that excitation light may readily penetrate the composition and emitted light be transmitted therefrom. The matrix is preferably a macromolecular hydrophobic polymer that is substantially insoluble in the aqueous fluid of interest, with sufficient structural integrity that it may be directly exposed to the fluid. Such polymers include, for example, cellulosic materials, high molecular weight or crosslinked polyvinyl alcohol (PVA), polyurethanes, quaternized polystyrenes, sulfonated polystyrenes, polyacrylamides, polyamides, polyesters, and mixtures thereof. Most preferably, the matrix is a polyamide or some other polymer with similar properties of permeability, optical transparency, and coating ability.

Any convenient fluorescent indicator that provides a signal that varies in response to the concentration of chlorinated aromatic compounds in an aqueous fluid may be used in the composition, provided that the indicator has no substantial detrimental effect on the matrix or the fluid being monitored. Preferably, the indicator is not affected by other chemical species that may be present in the fluid. Most preferably, the indicator is 8-amino-2-naphthalene sulfonate, which fluoresces in the presence of chlorinated aromatic compounds, including polychlorinated biphenyl compounds (PCBs).

The indicator is added to the uncured matrix material before polymerization takes place. The indicator is bonded physically or chemically to the material during the polymerization process, preferably uniformly distributed and chemically entrapped in the cured polymer matrix. The resulting composition is stable and substantially insoluble in the fluid, so it may be contacted directly with the fluid without loss of the indicator therefrom. The indicator is supplied in an amount sufficient to provide a concentration-dependent signal of sufficient intensity to be analyzed in determining the concentration of chlorinated aromatic compounds in the fluid of interest. The amount employed, therefore, varies depending on the specific indicator being used, the choice of matrix material, the other components of the measuring system including the light source and detector, and the expected concentration of chlorinated aromatics in the fluid.

By way of example, a composition for detecting the presence and concentration of chlorinated aromatic compounds, including PCBs, in an aqueous fluid includes a polyamide matrix and 8-amino-2-naphthalene sulfonate used as an indicator. The 8-amino-2-naphthalene sulfonate indicator can be derived from the corresponding sulfonic acid or the corresponding sulfonate salt. The indicator is present in an amount preferably less than approximately 1 wt. % of the composition, and most preferably less than approximately 0.1 wt. %. The formulation of the composition depends on the expected concentration of chlorinated aromatics in the fluid of interest: the lower the concentration, the higher the concentration of 8-amino-2-naphthalene sulfonate needed to provide a measurable signal; the higher the concentration, the lower the concentration of 8-amino2-naphthalene sulfonate. The amount of the composition needed for an effective measurement also depends on the concentration of chlorinated aromatics in the fluid of interest. Thus, lesser amounts of compositions with lower concentrations of 8-amino- 2-naphthalene sulfonate are needed for industrial process applications and in-tank monitoring; larger amounts of compositions containing more 8-amino-2-naphthalene sulfonate are needed for environmental applications such as groundwater monitoring where the PCB concentrations may be low.

Referring now to FIG. 1, there is shown a schematic view of an optical probe for measuring the concentration of chlorinated aromatic compounds in an aqueous fluid. In the following description similar components are referred to by the same reference numeral in order to simplify the understanding of the sequential aspect of the drawings.

Optical probe 10 has a slender, hollow, generally cylindrical housing 12 having a distal end 14 and a proximal end (shown generally as 16). Housing 12 is preferably made of a durable, non-corrosive material such as stainless steel, but can be made of any material suitable for carrying the internal components (shown in the Figures and discussed below)needed for operation of probe 10.

A plurality of openings 20, 22 are formed in distal end 14 of housing 12. Openings 20, 22 allows fluid to enter and exit the interior of housing 12. If desired, openings 20, 22 may be covered by screens 24, 26, respectively, in order to prevent foreign matter contained in the fluid from entering housing 12, possibly lodging in housing 12 and decreasing the operational effectiveness of probe 10. Screens 24, 26 are preferably made of a mesh material sufficient to allow the fluid of interest easy access into and out of the interior of housing 12, yet sturdy enough and of sufficiently fine mesh to prevent the entry of foreign matter such as dirt and grit. Openings 20, 22 are dimensioned to allow adequate flow of fluid into cavity 30 of housing 12. In order to allow fluid to flow into and out of cavity 30, probe 10 preferably has at least two openings 20, 22 as shown in FIGS. 1 and 2A. It will be understood that probe 10 may bear any convenient number of openings without departing from the spirit of the present invention.

The interior of housing 12 contains first optical fiber 32, second optical fiber 34, and sensor 36 to be described below (FIGS. 1, 2B). Optical fibers 32 and 34 are preferably aligned axially along the interior of housing 12. Distal end 14 of housing 12 bears reflector 38 spaced apart from sensor 36. Reflector 38 is made of stainless steel or other material suitable for reflecting light.

Fibers 32, 34 are any convenient type of small-diameter optical fiber that is capable of passing light therethrough. By way of example, the fibers may range in diameter between approximately 5 and 500 microns. Fibers 32, 34 may be the familiar type of fiber having a discrete core that transmits light and a cladding that refracts light. Alternatively, fibers 32, 24 may be stepped-index or graded-index fibers such as are known in the art.

If desired, the orientation of fibers 32, 34 with respect to each other is maintained by first spacer 40 that completely surrounds fibers 32 and 34 (FIG. 2C). Spacer 40 may be made of rubber or some other material suitable for maintaining the spacing between fibers 32 and 34 along the interior of housing 24.

Second spacer 42 maintains the separation of optical fibers 32, 34 with respect to housing 24 (FIGS. 2B, 2C). Spacer 42 may be made of rubber or other suitable material for properly maintaining separation. Alternatively, spacer 42 may be simply an extension or thicker segment of housing 12.

Sensor 36 is carried by distal ends 44, 46 of fibers 32, 34, respectively, as best seen in FIG. 1. Sensor 36 is formed of a composition according to the present invention, having a polymer matrix and a fluorescent indicator for detecting chlorinated aromatic compounds as described above. Thus, for measuring the concentration of PCBs in an aqueous fluid, sensor 36 comprises 8-amino-2-naphthalene sulfonate in a polyamide matrix. The 8-amino-2-naphthalene sulfonate indicator can be derived from the corresponding sulfonic acid or the corresponding sulfonate salt.

As noted above, the indicator is added to the uncured polymer solution before polymerization takes place. Sensor 36 may therefore be formed by simply dipping ends 44, 46 of optical fibers 32, 34 into the uncured solution, forming a thin, fast-drying coating on the ends. Once cured, such a polymer coating is on the order of 0.1 mm thick and provides a sufficient amount of the composition for use in detecting PCBs. It will be understood, however, that the thickness of the coating forming sensor 36 will vary depending on the particular choice of polymer, the choice and amount of indicator, and so forth. Additional layers may be formed on ends 44, 46 if a thicker coating is desired. Alternatively, the uncured composition is polymerized and sensor 36 fabricated by cutting a suitably-sized portion for use in probe 10. Virtually any type of sensor geometry may be used, including a sphere, disc, or cylinder formed of the composition. Such a sensor may be attached or otherwise bonded to ends 44, 46 of optical fibers 32, 34, or secured in housing 12 proximate to ends 44, 46.

In use, distal end 14 of probe 10 is placed in an aqueous fluid whose PCB concentration is to be measured. The fluid enters cavity 30 generally between sensor 36 and reflector 38, and contacts sensor 36. Excitation light of a specific wavelength is directed from a source (not shown) to sensor 36 by first optical fiber 32. This excitation signal is designed to cause the indicator carried by sensor 36 to fluoresce and thereby emit a signal having an intensity that depends on the concentration of PCBs in the fluid. The light is transmitted through the fluid in cavity 30, and is reflected back to second optical fiber 34 by reflector 38. Emission light entering second optical fiber 34 is transmitted to a detection and analysis system such as a spectrophotometer (not shown), where it is processed and analyzed using well known techniques to determine the PCB concentration of the fluid. As will be evident to one of ordinary skill, the level of the light signal measured by the detector may readily be calibrated to indicate the concentration of PCBs within the fluid.

Used as described above, the composition of the present invention provides a stable, rapid-response fluorescence indicator for measurement of the PCB concentration of an aqueous fluid. Variations in PCB concentration result in corresponding variations in the measured fluorescence signal, so sensor 36 is responsive to its operating environment and may be left in situ for long-term monitoring. Alternatively, probe 10 and sensor 36 may be cleaned between measurements, for example, by flushing cavity 30 with water. Probe 10 can then be used to make a series of measurements in different fluids, such as series of samples in an analytical laboratory. The composition is capable of detecting PCB concentration at levels as low as 1 ppb or less, rendering it suitable for environmental monitoring applications.

A composition according to the present invention may be used in an optical probe such as the probe described in Commonly-Assigned patent application Ser. No. 08/012,865, filed Feb. 3, 1993, entitled Fiber Optic Probe for Organic Species Determination. In this embodiment, optical probe 50 includes a cylindrical housing 52 having distal end 54 and proximal end 56. Similarly to housing 12 of probe 10, housing 52 is made of a durable, non-corrosive material such as stainless steel.

A plurality of openings are formed in distal end 54 of housing 52, covered by screens 60, 62, 64, 66. Screens 60, 62, 64, 66 allow the aqueous fluid of interest to enter and exit cavity 70 of housing 52, but prevent foreign matter such as dirt or grit from entering cavity 70.

The interior of housing 52 contains first optical fiber 72, second optical fiber 74, focusing lens 76, sensor 78, and reflector 80. The orientation of fibers 72 and 74 with respect to each other is maintained by first spacer 82, analogous to first spacer 40 of probe 10 as described above. Spacer 82 completely surrounds fibers 72 and 74 in order to maintain the spacing between the fibers along the interior of housing 52. Second spacer 84, analogous to second spacer 42 of probe 10, maintains the separation of optical fibers 72 and 74 with respect to housing 52.

Lens 76 is spaced apart from fibers 72 and 74 within cavity 70. Lens 76 is preferably made of glass or some other suitable optically-transparent material, and is dimensioned to fit snugly within the radial spacing of cavity 70. Lens 76 is positioned to focus and direct light from first optical fiber 72 through sensor 78 towards reflector 80. The position of lens 76 in cavity 70 also allows light traveling away from reflector 80 to be directed toward second optical fiber 74.

Sensor 78 is positioned distal to lens 76 in cavity 70. Sensor 78 is a solid disc formed of the composition described above, preferably substantially optically transparent to the excitation and emission wavelengths of the indicator, and at least partly permeable to the aqueous fluid of interest. Sensor 78 is positioned in cavity 70 so that light is directed by lens 76 through sensor 78 to reflector 80, and light reflected by reflector 80 passes through sensor 78 and is directed by lens 76 to second optical fiber 74.

Probe 50 is used in a similar manner to probe 10. Distal end 54 is placed in the aqueous fluid of interest so that the fluid can enter cavity 70 generally between lens 76 and reflector 54. Sensor 78 is at least partly permeable to the fluid, therefore, the fluid entering through any one of screens 60, 62, 64, 66 may exit through the same or another screen, depending on the direction of flow of the fluid.

Once distal end 54 of probe 50 is positioned for the measurement, the fluid entering cavity 70 interacts with the indicator contained in sensor 78. Excitation light from a remote source (not shown) is transmitted by first optical fiber 72 to lens 76, which focuses and directs the light to sensor 78. The light passing through sensor 78 travels to reflector 80, which reflects the light away from distal end 54 towards lens 76, sensor 78, and second optical fiber 74. Second fiber 74 transmits the light to a spectrophotometer or other detector (not shown) for analysis.

It will be apparent to those skilled in the art that many changes and substitutions can be made to the preferred embodiment herein described without departing from the spirit and scope of the present invention as defined by the appended claims.

What is claimed is:

1. A composition for detecting the presence of chlorinated aromatic compounds in an aqueous fluid, said composition comprising:
   a hydrophobic polymer matrix, said matrix being at least partly permeable to said fluid; and
   a fluorescent indicator including 8-amino-2-naphthalene sulfonate dispersed throughout said matrix, said indicator providing an optical signal which varies in response to the concentration of chlorinated aromatic compounds in said fluid.

2. The composition as recited in claim 1, wherein said indicator includes said 8-amino-2-naphthalene sulfonate in an amount less than approximately 1 wt. % of said composition.

3. The composition as recited in claim 1, wherein said indicator includes said 8-amino-2-naphthalene sulfonate in an amount less than approximately 0.1 wt. % of said composition.

4. The composition as recited in claim 1, wherein said matrix is made of polyamide.

5. An apparatus for measuring the concentration of chlorinated aromatic compounds in an aqueous fluid, said apparatus for use with a source of light and a spectrophotometer, said apparatus comprising:
   a housing having an interior, said housing having holes formed therein for receiving said fluid into said interior;
   means positioned in said housing for fluorescing, said fluorescing means fluorescing in response to the presence of chlorinated aromatic compounds in said fluid in said interior, said fluorescing means including
     a hydrophobic polymer matrix, said matrix being at least partly permeable to said fluid, and
     a fluorescent indicator dispersed throughout said matrix, said indicator including 8-amino-2-naphthalene sulfonate;
   a first optical fiber in spaced relation to said fluorescing means, said first fiber transmitting light from said source to said fluorescing means; and
   a second optical fiber in spaced relation to said fluorescing means, said second fiber transmitting light from said fluorescing means to said spectrophotometer.

6. The apparatus as recited in claim 5, further comprising a reflector spaced apart from said first and said second optical fibers, said fluorescing means positioned between said first and said second optical fibers and said reflector, said reflector reflecting light frown said first optical fiber to said second optical fiber after said light has passed through said fluorescing means.

7. The apparatus as recited in claim 5, wherein said first optical fiber and said second optical fiber each has an end, and wherein, said matrix is carried on said ends, said matrix applied to said ends by dipping said ends in an uncured mixture of said polymer and said indicator.

8. The apparatus as recited in claim 5, wherein said matrix further comprises polyamide.

9. The apparatus as recited in claim 5, wherein said matrix contains said 8-amino-2-naphthalene sulfonate in an amount less than approximately 1 wt. % of said fluorescing means.

10. The apparatus as recited in claim 5, wherein said matrix contains said 8-amino-2-naphthalene sulfonate in an amount less than approximately 0.1 wt. % of said fluorescing means.

\* \* \* \* \*